(12) United States Patent
Bailey

(10) Patent No.: US 10,842,581 B2
(45) Date of Patent: Nov. 24, 2020

(54) PANEL AND DRAPE FOR INPUT CONTROL CONSOLE OF ELONGATE DEVICE

(71) Applicant: INTUITIVE SURGICAL OPERATIONS, INC., Sunnyvale, CA (US)

(72) Inventor: David W. Bailey, Portola Valley, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/677,278

(22) Filed: Nov. 7, 2019

(65) Prior Publication Data

US 2020/0069388 A1 Mar. 5, 2020

Related U.S. Application Data

(63) Continuation of application No. 16/049,640, filed on Jul. 30, 2018, now Pat. No. 10,512,515.
(Continued)

(51) Int. Cl.
*A61B 34/00* (2016.01)
*G06F 3/0362* (2013.01)
(Continued)

(52) U.S. Cl.
CPC ........ *A61B 34/74* (2016.02); *A61B 17/00234* (2013.01); *A61B 34/25* (2016.02);
(Continued)

(58) Field of Classification Search
CPC .... A61B 17/00234; A61B 2017/00199; A61B 2017/00314; A61B 2034/2051;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

WO WO-2016025465 A1 2/2016
WO WO-2018005680 A1 1/2018
WO WO-2018005928 A1 1/2018

OTHER PUBLICATIONS

Co-pending U.S. Appl. No. 62/357,258, filed Jun. 30, 2016.
(Continued)

*Primary Examiner* — Marnie A Matt
(74) *Attorney, Agent, or Firm* — Haynes and Boone, LLP

(57) ABSTRACT

Systems and methods for controlling an elongate device include a console. The console includes a first recess and a removable first input control for controlling motion of the medical device. The console also may include one or more first sensors located about the first recess that detect motion of the first input control and detect operator contact with the first input control. The console also may include an integrated display screen arranged to display status information for the medical device. In some embodiments, the first input control controls an insertion depth or steering of the medical device, and may be in the form of a scroll wheel forming a part of a removable control assembly.

20 Claims, 13 Drawing Sheets

Related U.S. Application Data

(60) Provisional application No. 62/539,467, filed on Jul. 31, 2017.

(51) Int. Cl.
*G06F 3/0354* (2013.01)
*A61B 17/00* (2006.01)
*A61B 46/10* (2016.01)
*A61B 34/37* (2016.01)
*A61B 34/20* (2016.01)
*A61B 34/30* (2016.01)
*A61B 90/00* (2016.01)

(52) U.S. Cl.
CPC .............. *A61B 34/37* (2016.02); *A61B 46/10* (2016.02); *G06F 3/0362* (2013.01); *G06F 3/03549* (2013.01); *A61B 2017/00199* (2013.01); *A61B 2017/00314* (2013.01); *A61B 2034/2051* (2016.02); *A61B 2034/2057* (2016.02); *A61B 2034/2061* (2016.02); *A61B 2034/301* (2016.02); *A61B 2090/365* (2016.02); *A61B 2090/371* (2016.02)

(58) Field of Classification Search
CPC .... A61B 2034/2057; A61B 2034/2061; A61B 2034/301; A61B 2090/365; A61B 2090/371; A61B 34/25; A61B 34/37; A61B 34/74; A61B 46/10; G06F 3/03549; G06F 3/0362
USPC ........................................................ 606/130
See application file for complete search history.

(56) References Cited

U.S. PATENT DOCUMENTS

| | | |
|---|---|---|
| 7,316,681 B2 | 1/2008 | Madhani et al. |
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 2006/0013523 A1 | 1/2006 | Childlers et al. |
| 2007/0185404 A1 | 8/2007 | Hauck et al. |
| 2009/0105597 A1 | 4/2009 | Abraham |
| 2009/0248039 A1* | 10/2009 | Cooper .................. A61B 34/30 606/130 |
| 2010/0160786 A1 | 6/2010 | Nordgren et al. |
| 2011/0152882 A1 | 6/2011 | Wenderow et al. |
| 2012/0071752 A1 | 3/2012 | Sewell et al. |
| 2013/0257718 A1 | 10/2013 | Oejelund et al. |
| 2016/0374775 A1* | 12/2016 | Prpa ...................... A61B 90/96 705/3 |
| 2019/0029770 A1 | 1/2019 | Bailey et al. |
| 2019/0226577 A1* | 7/2019 | Lalchandani ....... F16H 59/0213 |

OTHER PUBLICATIONS

Co-pending U.S. Appl. No. 62/486,879, filed Apr. 18, 2017.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

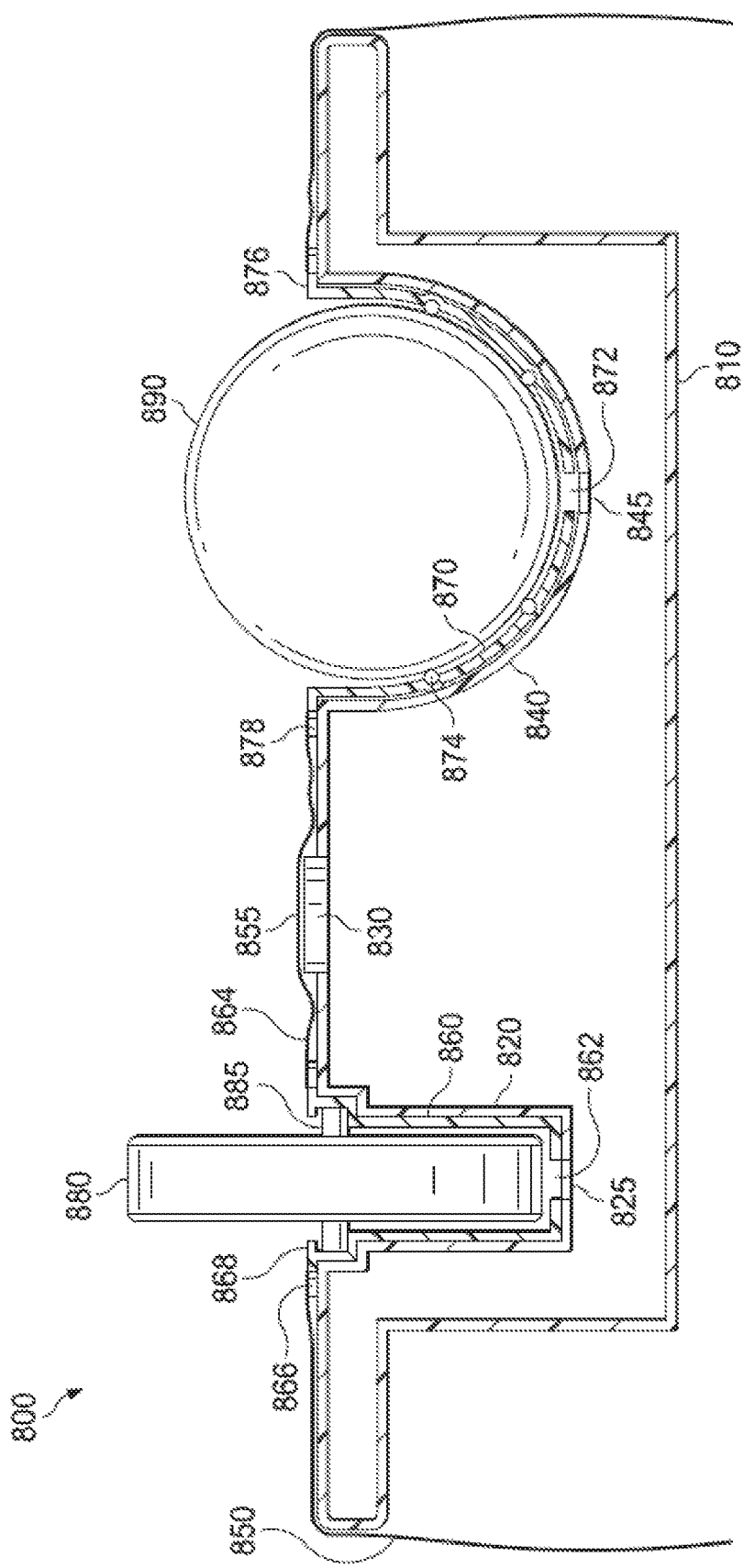

PANEL AND DRAPE FOR INPUT CONTROL CONSOLE OF ELONGATE DEVICE

CROSS-REFERENCE TO RELATED APPLICATIONS

This patent application is a continuation of U.S. patent application Ser. No. 16/049,640, filed Jul. 30, 2018, which claims the benefit of the filing date of U.S. Provisional Application No. 62/539,467 filed Jul. 31, 2017, which are incorporated by reference herein in their entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Accordingly, it would be advantageous to provide input controls that support intuitive control and management of flexible and/or steerable elongate devices, such as steerable catheters, that are suitable for use during minimally invasive medical techniques.

SUMMARY

The embodiments of the invention are best summarized by the claims that follow the description.

Consistent with some embodiments, an input control system for a medical device may include a console that includes a first recess and a first input control for controlling motion of the medical device. The first input control may be removeably held within the first recess to provide access to the first recess and the first input control is removable from the first recess for cleaning.

The console also may include one or more first sensors located about the first recess. The one or more first sensors may detect motion of the first input control and detect operator contact with the first input control. The console also may include an integrated display screen arranged to display status information for the medical device.

Consistent with some embodiments, a method for controlling a medical device, the method performed by an input console may include detecting, over a first period of time, a continuous motion of a first input control removeably held within a first recess of the input control console and operator contact with the first input control during at least part of the continuous motion of the first input control. The method may also include controlling, based on the detecting of the continuous motion of the first input control, an insertion depth or steering of the medical device and displaying, on an integrated display screen of the input console, status information for the medical device.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 8 is a simplified front cut-away view of an input control console according to some embodiments.

FIGS. 9A, 9B, 10A, and 10B are simplified diagrams of input control moldings according to some embodiments.

Figure 11:
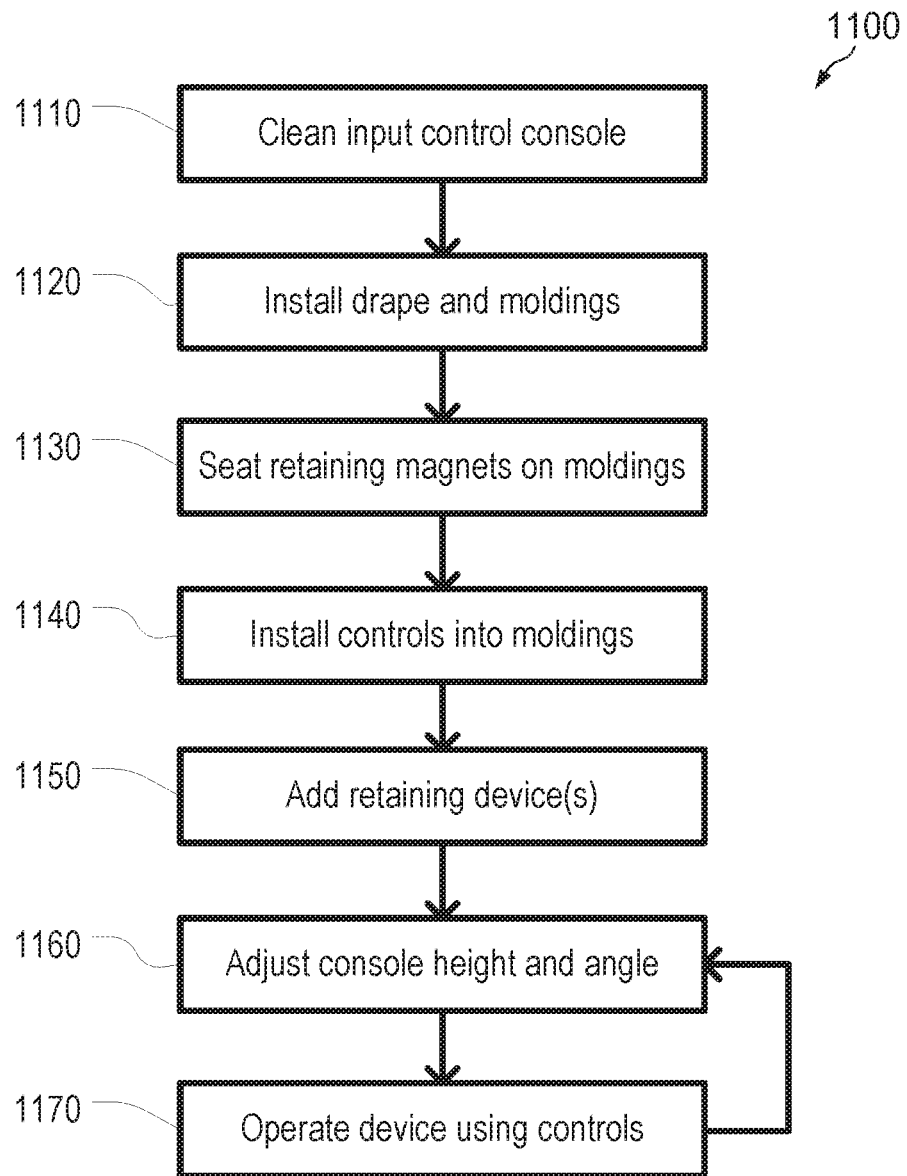

FIG. 11 is a simplified diagram of a method of preparing and using an input control console according to some embodiments.

Figure 12:
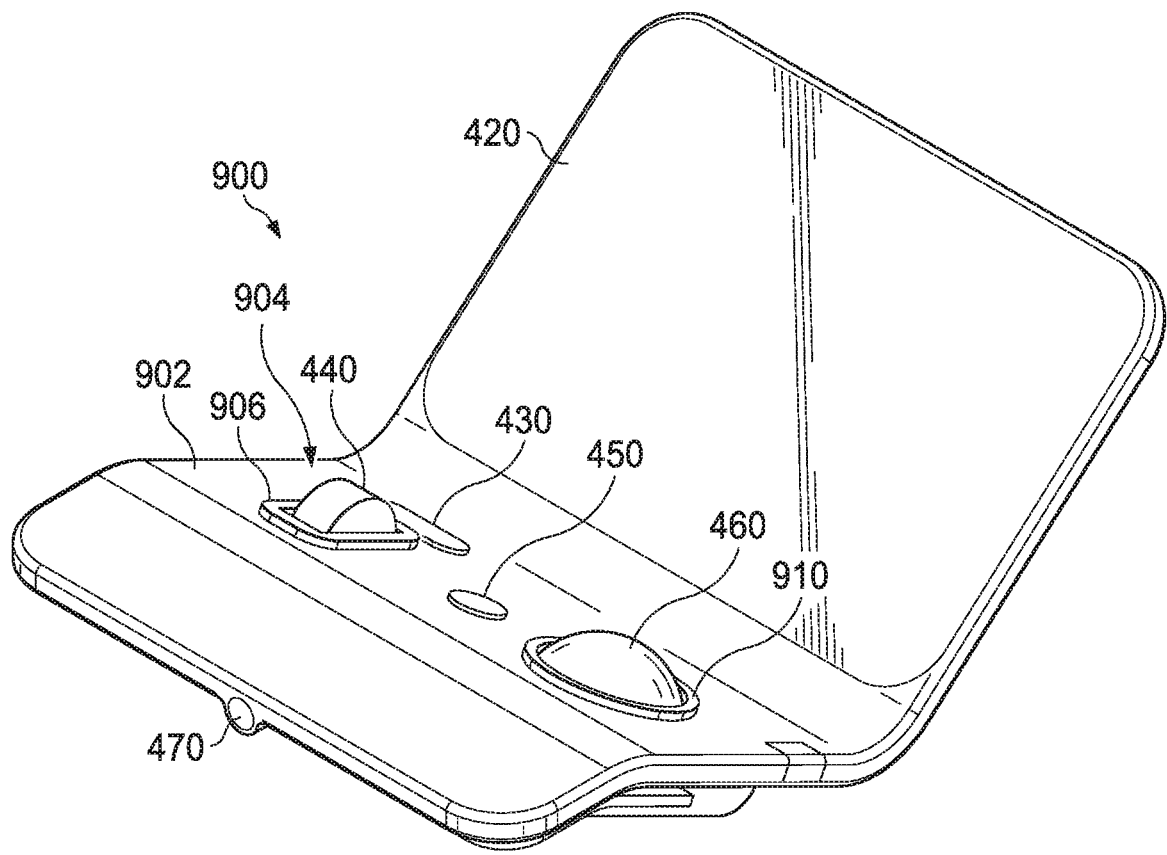

FIG. 12 is a simplified diagram of another input control console according to some embodiments.

Figure 13:
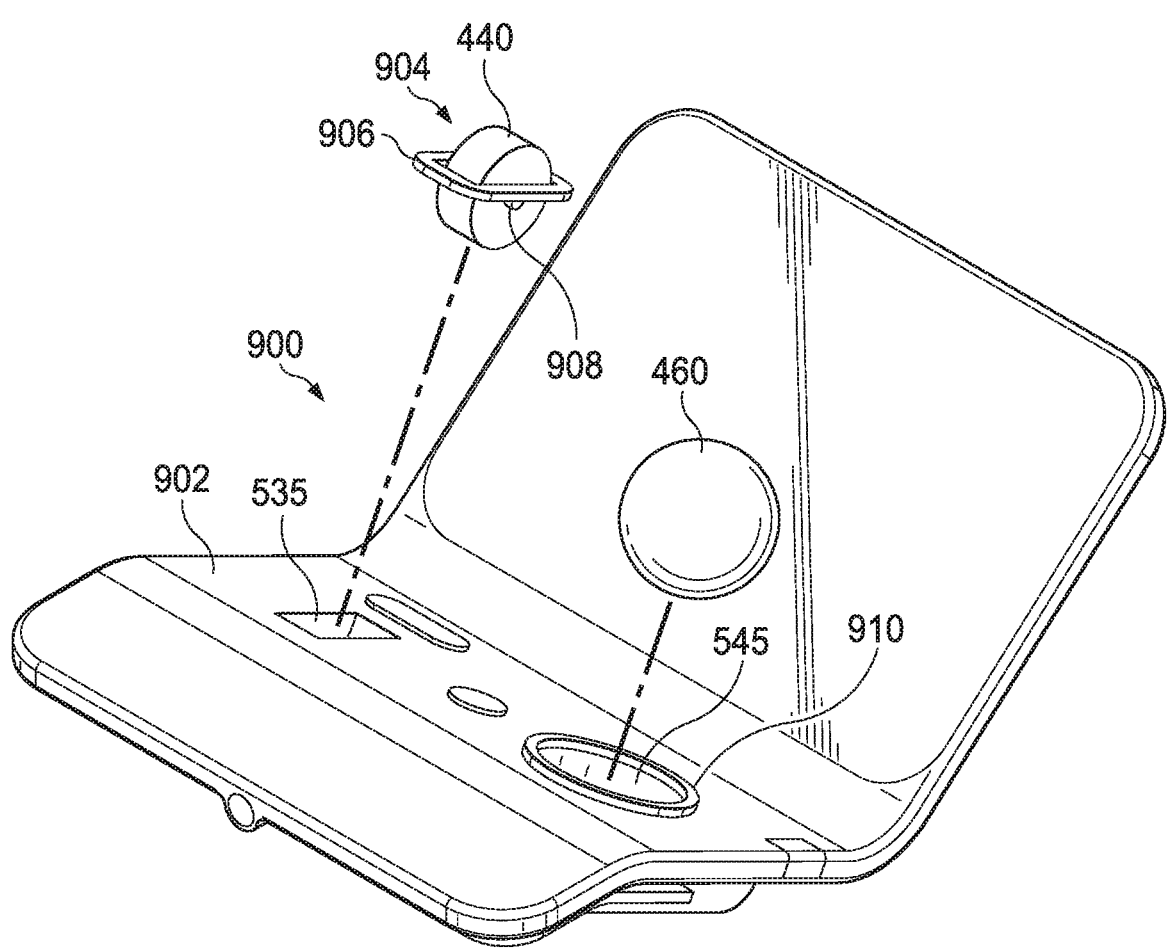

FIG. 13 is a simplified diagram of the input control console of FIG. 12 with some removable input controls displaced according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
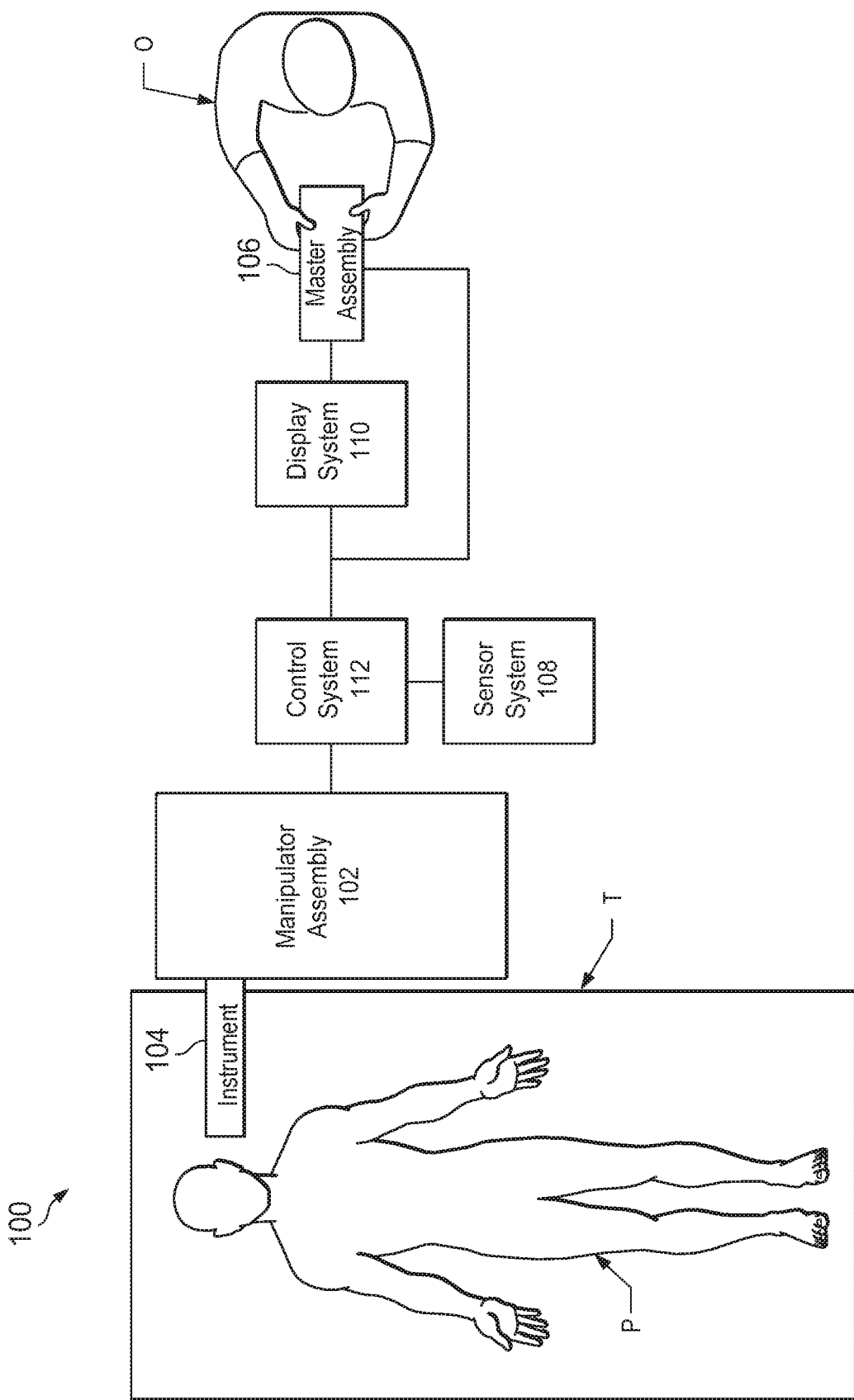
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, a physician, or other health care provider, as illustrated in FIG. 1) to view the interventional site and to control teleoperational manipulator assembly 102.

Master assembly 106 may be located at a physician's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence. In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit air and/or other gasses or liquids to clean the one or more lenses. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
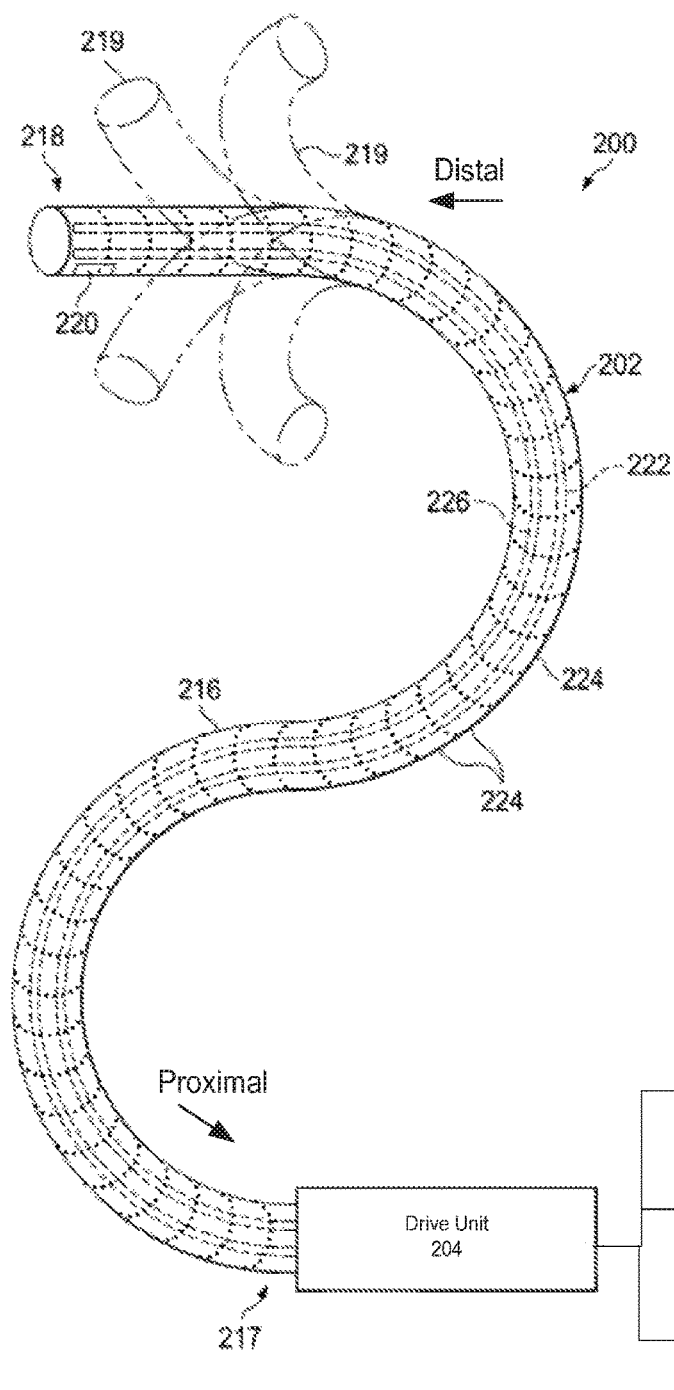
FIG. 2A is a simplified diagram of a medical instrument system according to some embodiments.
Figure 2B:
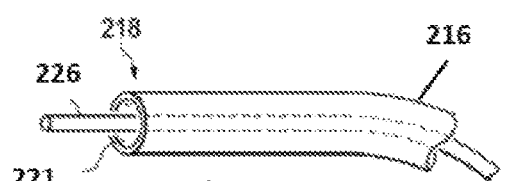
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. Medical instrument system 200 includes elongate device 202, such as a flexible catheter, coupled to a drive unit 204. Elongate device 202 includes a flexible body 216 having proximal end 217 and distal end or tip portion 218. Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224.

Medical instrument 226 may additionally house cables, linkages, or other actuation controls (not shown) that extend between its proximal. and distal ends to controllably bend the distal end of medical instrument 226. Steerable instruments are described in detail in U.S. Pat. No. 7,316,681 (disclosing "Articulated Surgical Instrument for Performing Minimally Invasive Surgery with Enhanced Dexterity and Sensitivity") and U.S. Pat. No. 9,259,274 (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right"

steering to control a yaw of distal end 281. Steerable elongate devices are described in detail in U.S. Pat. No. 9,452,276 (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

Figure 3A:
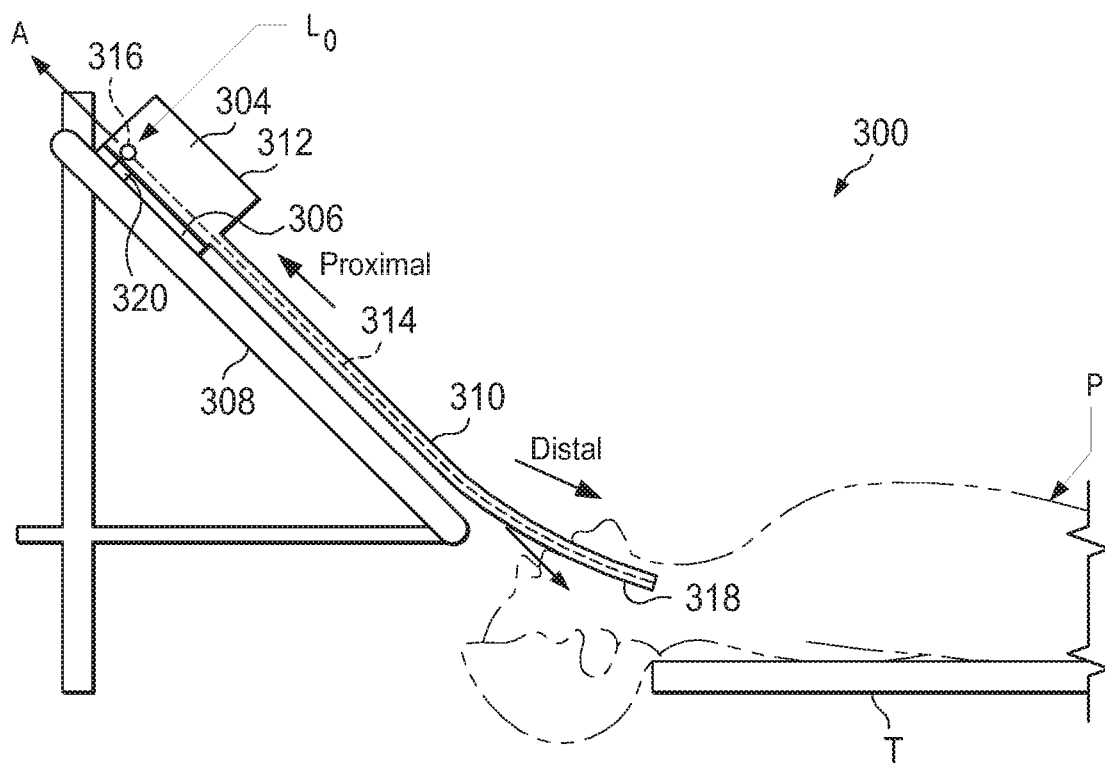
FIGS. 3A and 3B are simplified diagrams of side views of a patient coordinate space including a medical instrument mounted on an insertion assembly according to some embodiments.
Figure 3B:
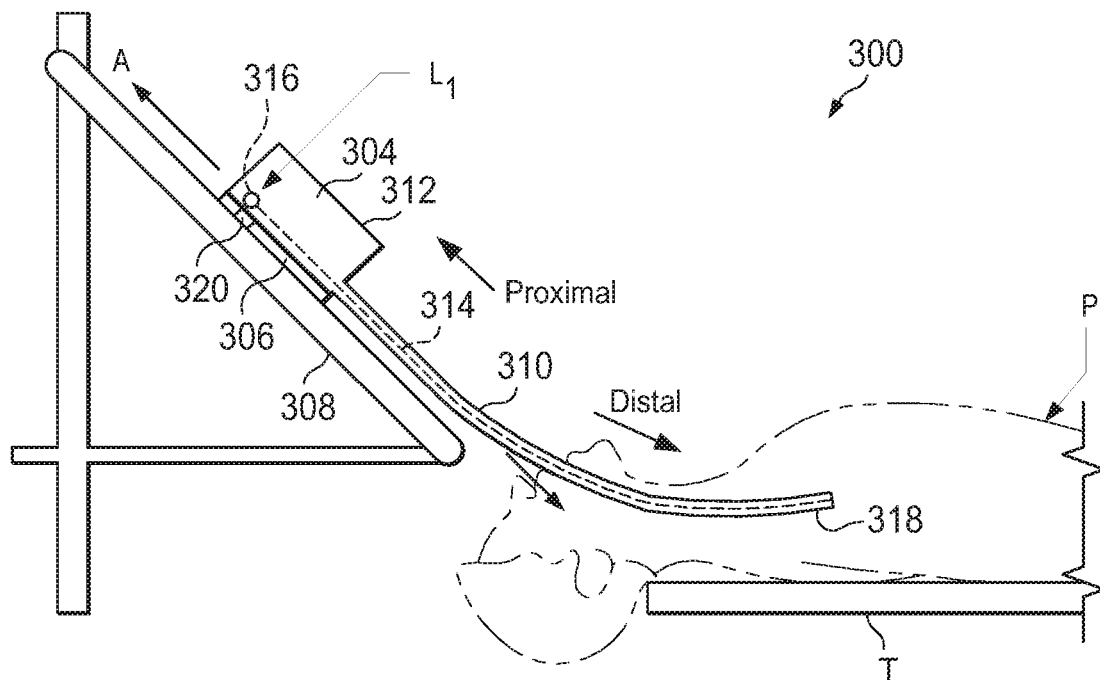

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Instrument carriage 306 is mounted to an insertion stage 308 fixed within surgical environment 300. Instrument carriage 306 or insertion stage 308 may include actuators, such as servomotors, (not shown) that control motion of instrument carriage 306 along insertion stage 308.

FIG. 3A shows instrument body 312 and instrument carriage 306 in a retracted position along insertion stage 308. With this retracted position of instrument body 312 and instrument carriage 306, distal end 318 of elongate device 310 may be positioned just inside an entry orifice of patient P.

Control of a flexible elongate device such as elongate device 202 having flexible body 216, elongate device 310, and/or a flexible catheter often involves the simultaneous control of multiple degrees of freedom. In some examples, to control insertion and/or retraction of the elongate device and correspondingly an insertion depth of the distal end of the elongate device, such as distal end 218 and/or 318, one or more actuators, such as the one or more actuators controlling the position of instrument carriage 306 along insertion stage 308, are used. Commands to the one or more actuators may be received from operator O using a single degree of freedom input control, such as a lever, joystick, and/or the like. In some examples, to control the steering of the distal end, the steering unit for the distal end, such as drive unit 204, is provided with both pitch and yaw instructions. The pitch and yaw instructions may be received from operator O using a two-degree of freedom input control, such as a joystick. Because control of the elongate device typically includes concurrently providing insertion and/or retraction instructions along with steering instructions, the input controls for insertion and/or retraction and steering are typically separate from each other.

For certain procedures, the use of levers and/or joysticks as the input controls for the elongate devices of FIGS. 2A, 3A, and/or 3B can be less than ideal. This is because levers and joysticks are input controls that have a finite length of travel, which are often disproportionately short relative to the length of insertion travel and/or the range of steering necessary to access certain anatomy. Thus, use of the levers and/or joysticks as positional input devices that provide a limited insertion depth, pitch setting, and/or yaw setting can be inadequate. Input controls with a finite length of travel are typically used as velocity input devices where either movement of the input control either specifies three velocity settings (reverse, idle, and forward) for switch-type input controls or variable velocity settings for proportional type input controls. However, velocity-based control of the insertion depth, pitch setting, and/or yaw setting is often unsatisfactory for high-precision manipulation of the elongate device as the control of the velocity of the distal end does not generally intuitively correspond with desires to make small high-precision changes in the insertion depth, pitch setting, and/or yaw setting, which is typically required for teleoperated minimally invasive medical procedures.

In contrast, input controls offering an infinite length of travel can offer better options as input controls for the elongate device when accessing certain anatomy. Input controls with an infinite length of travel correspond to input controls that allow continued movement of the inputs controls in a particular direction where no stop, such as a mechanical stop, restricts further movement. One example of a one degree of freedom input control with an infinite length of travel is a scroll wheel, which may be spun unendingly in either direction. One example of a multiple-degree of freedom input control with an infinite length of travel is a track ball, which may be spun unendingly about any number of axes, which in practice may be decomposed into combinations of a left and right rotation, a forward and back rotation, and a spin in place rotation. Other examples, of input controls that support an apparent infinite length of travel are input controls that support directional swipes without movement of the input control. Examples of directional swipe input controls are touch pads, touch screens, and/or the like.

Accordingly, it would be advantageous to develop input control units for elongate devices to provide input controls having infinite length of travel along with additional input controls to support the various modes of operation for elongate device.

Figure 4A:
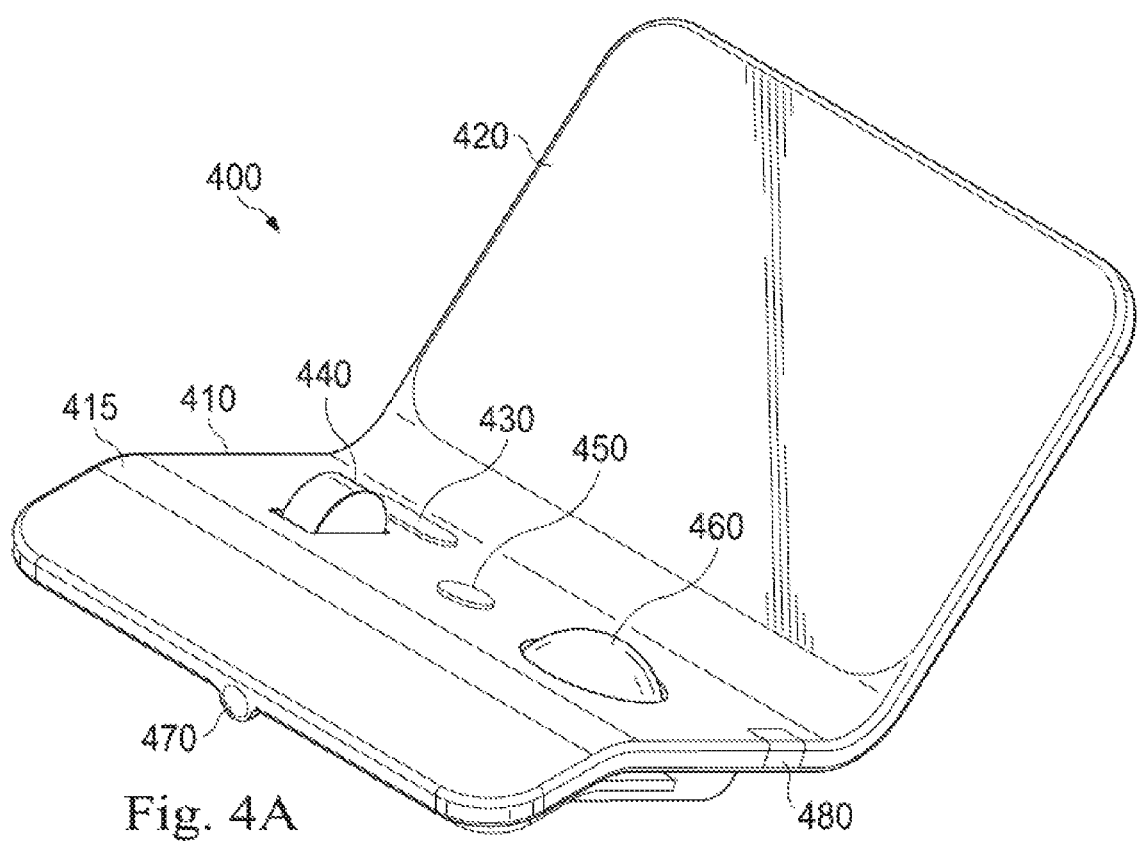
FIGS. 4A and 4B are simplified perspective diagrams of another input control console according to some embodiments.
Figure 4B:
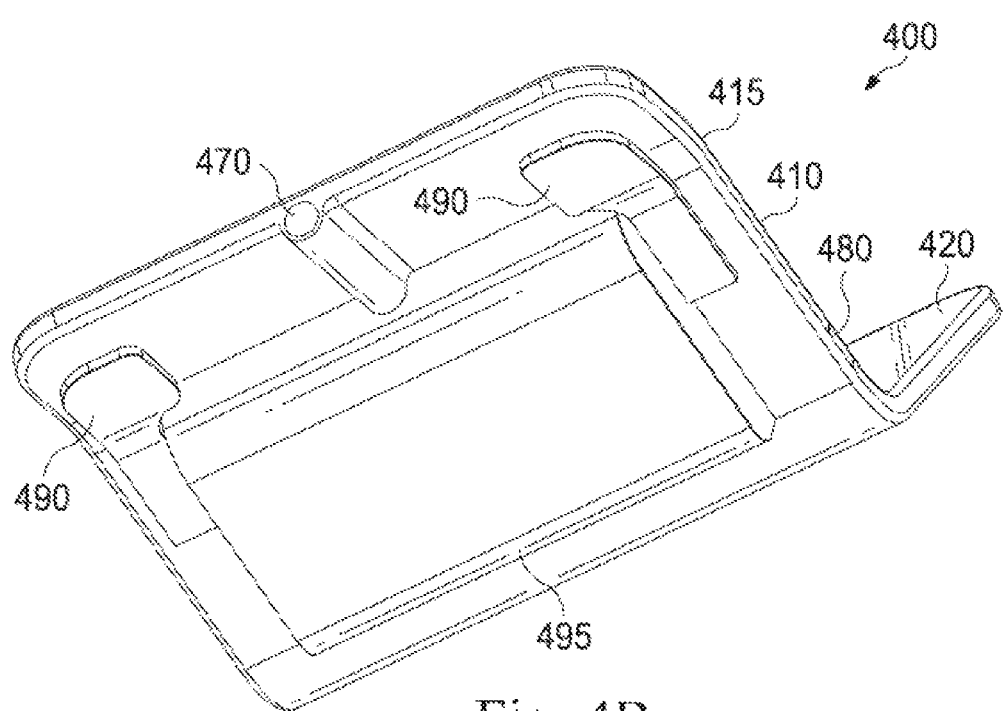

FIGS. 4A and 4B are simplified perspective diagrams of an input control console 400 according to some embodiments. FIG. 4A shows a top view of input control console 400 and FIG. 4B shows a bottom view of input control console 400. A top surface of input control console 400, further includes various input controls including a camera cleaning button 430, an insertion/retraction control 440, a passive control button 450, and a steering control 460. Although FIGS. 4A and 4B show configurations of the various input controls for an elongate device, it should be understood that input control console 400 can control any variety of instruments and devices and the exact placement, orientation, relative-positioning, and/or the like of the various input controls are exemplary only. It is understood that other configurations of input controls, different numbers of input controls, and/or the like are possible. In some embodiments, input control console 400 is suitable for use as a patient-side input control unit for the elongate device and may, for example, be mounted in proximity to insertion stage 308.

Although not shown in FIGS. 4A and 4B, input control console 400 may optionally include one or more circuit boards, logic boards, and/or the like that are usable to provide power, signal conditioning, interfacing, and/or other circuitry for input control console 400. In some examples, the one or more circuit boards, logic boards, and/or the like are useable to steer input control console 400 and its various input controls to a control unit for the elongate device. In some examples, the control unit of the elongate device corresponds to the control device of master assembly 106, control system 112, and/or the like. In some examples, the one or more circuit boards, logic boards, and/or the like may include memory and one or more one or more processors, multi-core processors, field programmable gate arrays (FPGAs), application specific integrated circuits (ASICs), and/or the like. In some examples, the memory may include one or more types of machine-readable media. Some common forms of machine-readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

Input control console 400 includes a contoured body 410 configured to provide ergonomic support for the hands and/or wrists of an operator, such as operator O. As shown in FIGS. 4A and 4B, contoured body 410 has a "bent" or "curved" shape, which includes a bend point 415 located between the various input controls (discussed below) and the wrist rest, which is located toward the body of the operator. The location and amount of bend in bend point 415 may provide support and/or a resting surface for the wrists and/or the distal ends of the forearms of the operator at a different angle than the hands and fingers of the operator as the hands and fingers are used to operate the various input controls. As is discussed further below, the angle of contoured body 410 may be adjusted so that bend point 415 may be above, below, and/or aligned with a same relative height as the various input controls.

Input control console 400 further includes an integrated display screen 420. Screen 420 is mounted at an angle relative to the rest of input control console 400 to provide a view of information on screen 420 to the operator while the operator is using input control console 400. In some embodiments, screen 420 is optionally a touchscreen to allow the operator to interact and/or manipulate information displayed on screen 420, activate additional controls, and/or the like. In some examples, screen 420 is a capacitive touchscreen. In some examples, the information displayed on screen 420 may include a region with status information about the elongate device being controlled including information such as a model number, size, length, insertion depth, relative tension of the body of the elongate device, and/or the like. In some examples, the information displayed on screen 420 may include a region with an alignment and/or a traversal display mode. In some examples, the system is operating in the traversal mode when the distal end of the elongate device is a specified distance from a desired target, the desired target including a location chosen for a treatment of a patient anatomy. While in the traversal mode, a traversal view is displayed to the operator. The traversal view may optionally include a live endoscopic view from an endoscope located at the distal end of the elongate device as well as a full or partial model of the anatomy of the patient, with or without a suggested navigation path to the desired target for the elongate device superimposed. In some examples, the system is operating in the alignment mode when the distal end of the elongate device is near the target. While in the alignment mode, an alignment view is displayed to the operator. The alignment view may optionally include the live endoscopic view as well as targeting and/or alignment indicators to help the operator navigate the distal end to the target. In some examples, the targeting and/or alignment indicators may correspond to cross-hairs, a bull's eye, and/or the like. Further description of possible display modes and their features are provided in co-owned U.S. Patent Application Ser. No. 62/357,258 (filed Jun. 30, 2016) (disclosing "Graphical User Interface for Displaying Guidance Information in a Plurality of Modes During an Image-Guided Procedure") and co-owned U.S. Patent Application Ser. No. 62/486,879 (filed Apr. 18, 2017) (disclosing "Graphical User Interface for Monitoring an Image-Guided Procedure"), both of which are incorporated by reference herein in its entirety. In some examples, switching between the display modes may be accomplished using a button, slider, and/or similar control displayed on screen 420 and/or by automatic decision of control software depending upon a proximity of the distal end of the elongate device to a target.

In some examples, camera cleaning button 430 is a momentary push button, a momentary membrane switch, a momentary toggle switch, a momentary rocker switch, and/or the like for use in triggering cleaning of an imaging system, such as an endoscope located at the distal end of the elongate device being controlled by input control console 400. In some examples, camera cleaning button 430 may optionally include suitable labeling, icons, illumination, and/or the like. In some examples, activation of camera cleaning button 430 triggers the cleaning mechanisms of the endoscope to emit a puff of air and/or other gasses to blow one or more lenses of the endoscope clean. In some examples, the length of time camera cleaning button 430 is activated may control the amount of air and/or other gasses that are blown across the one or more lenses. In some examples, camera cleaning button 430 may include two or more activation positions, with each activation position delivering a different amount of air and/or other gasses or liquids across the one or more lenses.

In some examples, insertion/retraction control 440 is a single degree of freedom infinite length of travel input control providing infinite length of travel along a first axis usable by the operator to control the insertion depth of the distal end of the elongate device. Insertion/retraction control 440 is depicted as a scroll wheel, however, other types of input controls, including non-infinite length of travel input controls, are possible. In some examples, scrolling of the scroll wheel forward away from the operator increases the insertion depth (insertion) of the distal end of the elongate device and scrolling of the scroll wheel backward toward the operator decreased the insertion depth (retraction) of the distal end of the elongate device. In some examples, insertion/retraction control 440 is usable by the operator to move instrument carriage 306 in and out along insertion stage 308 in order to control the insertion depth of distal end 318. Some non-infinite length of travel input controls may include buttons, rocker switches, toggles, dials, and other input controls. These too may be arranged to provide insertion, retraction, and other control of the elongate device.

When insertion/retraction control 440 is an infinite length of travel input control, operating insertion/retraction control 440 in a position-specifying mode allows the operator to exercise precise insertion depth control of the distal end of the elongate device over the full length of travel of the elongate device. In some examples, movement of insertion/retraction control 440 may be detected by the one or more circuit boards, logic boards, and/or the like of input control console 400 using one or more encoders, resolvers, optical sensors, hall effect sensors, and/or the like (not shown). In some examples, feedback applied via one or more electromagnetic actuators, and/or the like may optionally be used to apply haptic feedback to insertion/retraction control 440. In some examples, a scale factor between an amount of movement of insertion/retraction control 440 and an amount of insertion and/or retraction movement by the elongate device is adjustable by the operator and/or control software of the elongate device so that an insertion/retraction velocity of the elongate device relative to an angular velocity of insertion/retraction control may be adjusted to allow both fast insertion and retraction when advantageous and slower more precise insertion and retraction when greater control precision is desired. In some embodiments, insertion/retraction control 440 may optionally be touch sensitive via capacitive touch detection) and/or have pressure sensitivity so that input control console 400 is able to differentiate between intended movement of insertion/retraction control 440 by the operator from inadvertent movement due to accidental contact, dropping of input control console 400, and/or the like.

In some embodiments, camera cleaning button 430 and insertion/retraction control 440 are located so as to be operable by the same hand. And, although camera cleaning button 430 and insertion/retraction control 440 are positioned for operation by the left hand of the operator, they could alternatively be located to the right side of input control console 400 for operation by the right hand of the operator.

In some examples, passive control button 450 is a momentary push button, a momentary membrane switch, a momentary toggle switch, a momentary rocker switch, and/or the like for use in placing the elongate device in a passive control mode. In some examples, passive control button may each optionally include suitable labeling, icons, illumination, and/or the like. In some examples, the passive control mode may include gradually reducing the stiffness of the elongate device (e.g., by reducing tension in the steering cables, such as by reducing a torque set point of corresponding actuators) as long as passive control button 450 is depressed. In some examples, the stiffness may be ramped down over a 0.2 to 2 second long period using a linear or other monotonic decreasing profile. In some examples, upon release of passive control button 450, the stiffness may be maintained at the current stiffness or allowed to ramp back to the stiffness prior to activation of passive control button 450. In some examples, a number of button presses in close succession, an amount of time passive control button 450 is depressed, an amount of pressure and/or a distance to which passive control button 450 is pressed may control one or more of a rate at which the elongate device becomes highly flexible, the extent of flexibility, a type or sub-mode of passive mode, and/or the like. Further discussion of different styles and/or types of passive mode and their operation and triggering may be found in co-owned International Patent Application PCT/US2017/40214, filed Jun. 30, 2017 (disclosing "Systems and Methods for Flexible Computer-Assisted Instrument Control"), which is incorporated by reference herein in its entirety.

In some examples, steering control 460 is a multi-degree of freedom infinite length of travel input control providing infinite length of travel about any number of axes, which in practice may be decomposed into combinations of a left and right rotation, a forward and back rotation, and a spin in place rotation. Steering control 460 is depicted as a track ball, however, other types of input controls, including non-infinite length of travel input controls, are possible. Steering control 460 is usable by the operator to concurrently control both the pitch and yaw of the distal end of the elongate device. In some examples, components of the track ball rotation in the forward and back directions may be used to control a pitch of the distal end of the elongate device and components of the track ball rotation in the left and right directions may be used to control a yaw of the distal end of the elongate device. In some examples, other rotational components of the track ball may be used to control pitch and/or yaw with the operator being optionally able to control whether the direction of rotation is normal and/or inverted relative to the direction applied to the steering (e.g., rotate forward to pitch down and backward to pitch up versus backward to pitch down and forward to pitch up). In some examples, steering control 460 is usable by the operator to manipulate the distances each of the cables that extend between the proximal and distal ends of the elongate device are pushed and/or pulled When steering control 460 is an infinite length of travel input control, operating steering control 460 in a position-specifying mode allows the operator to exercise precise steering of the distal end of the elongate device in both pitch and yaw concurrently so as to achieve precise control over an orientation of the distal end. In some examples, steering control 460 is usable by the operator to manipulate a desired bend angle of the distal ends of the elongate device. In some examples, the desired bend angle may then be used as a set point for the controller of the elongate device that controls the distances and/or forces by which each of the cables extending between the proximal and distal ends of the elongate device are pushed and/or pulled to obtain the desired bend angle in the distal end of the elongate device. In some examples, movement of steering control 460 rimy be detected by the one or more circuit boards, logic boards, and/or the like of input control console 400 using one or more encoders, resolvers, optical sensors, hall effect sensors, and/or the like (not shown). In some examples, feedback applied to the one or more electromagnetic actuators and/or the like may optionally be used to apply haptic feedback to steering control 460. In some examples, a scale factor between an amount of movement of steering control 460 and an amount of pitch and/or yaw imparted to the distal end of the elongate device is adjustable by the operator and/or control software of the elongate device. In some embodiments, steering control 460 may optionally be touch sensitive (e.g., via capacitive touch detection) and/or have pressure sensitivity so that input control console 400 is able to differentiate between intended movement of steering control 460 by the operator from inadvertent movement due to accidental contact, dropping of input control console 400, and/or the like.

Input control console 400 further includes an emergency stop button 470. In some examples, emergency stop button 470 may be wired as a normally closed switch that is directly coupled to the control unit for the elongate device and/or the actuators used to drive the elongate device so that the operator of the elongate device may quickly interrupt control of the elongate device and cause the elongate device to enter a fail-safe state. In some examples, other configurations for emergency stop button 470 are possible including using a two-pole switch with a normally closed pole and a normally open pole. When any combination of positions for the poles are different than normally closed/normally open (e.g., open/closed, closed/closed, and open/open) are detected, an emergency stop occurs. As shown, emergency stop button 470 is depicted as a recessed button mounted in a bezel that extends beyond the front of input control console 400, although other configurations, such as a mushroom head are possible. In some examples, emergency stop button 470 may optionally include one or more characteristics common to emergency stop buttons including a red coloration and/or the like. In some examples, emergency stop button 470 may optionally include suitable labeling, icons, and/or the like. In some examples, emergency stop button 470 may optionally be conditionally illuminated to indicate whether input control console 400 is properly connected to the elongate device, has been used to initiate an emergency stop, and/or the like.

In some embodiments, input control console 400 may optionally support a lock mode of operation. In the lock mode of operation, when input control console 400 detects loss of affirmative contact by the operator with insertion retraction control 440 and/or steering control 460, such as via the capacitive touch or pressure sensitive features of insertion/retraction control 440 and/or steering control 460, a rigidity of the elongate device may increase and/or insertion and/or retraction may be prevented. In the lock mode, a position and/or orientation of the distal end of the elongate device is maintained at the position and/or orientation detected before loss of affirmative contact was detected.

Input control console 400 further includes a data port 480. In some examples, data port 480 is a universal serial bus (USB) port, and/or the like. Data port 480 may be usable to import operator-specific, patient-specific, or procedure-specific data to input control console using, for example, a portable flash drive. In some examples, data port 480 may include an optional hinged door, flexible cap or insert, and/or the like to protect and/or seal data port 480 when data port 480 is not in use.

As shown in FIG. 4B, contoured body 410 is mounted to a base 495. Although not shown, base 495 may be an upper end of a cart, table, rack, stand and/or the like. Base 495 may support portability, installation, and/or mounting of input control console 400 in proximity to a patient, the actuation mechanisms for the elongate device, and/or the like. Input control console 400 further includes one or more paddle levers 490 usable to control a height and/or angle of input control console 400 relative to base 495 to allow each operator to adjust a height or orientation angle of input control console to a comfortable position and orientation for operation. In alternative embodiments (not shown), the one or more paddle levers 490 can be positioned near a floor and be configured as foot pedals at or near a lower portion of the cart, table, rack, or stand.

Although not shown, input control console 400 may further include one or more cables to couple the input control console 400 to a power supply, the control unit for the elongate device, and/or the like. In some examples, the one or more cables include a dedicated cable for connecting emergency stop button 470 to the fail-safe mechanisms of the elongate device. In some examples, the one or more cables include one or more buses and/or communication cables to allow the one or more circuit boards, logic boards, and/or the like of input control console 400 and the control unit of the elongate device to exchange commands, status information, and/or the like. In some examples, the one or more buses and/or communications cables may be compatible with a communication standard, such as USB, RS-232, RS-485, SCSI, CAN, GPIB, and/or the like. In some examples, the one or more buses and/or communication cables are coupled to the one or more circuit boards, logic boards, and/or the like using one or more transceivers. In some examples, the one or more buses and/or communication cables are optional and may be replaced with one or more wireless transceivers supporting wireless communication using one or more of near-field communication (NFC), Bluetooth™, IrDA, HomeRF, IEEE 802.11, DECT, and Wireless Telemetry and/or the like. Although not shown, input control console 400 may further include one or more self-contained power sources (e.g., one or more batteries) and/or include one or more coils for receiving power inductively.

Although not shown, input control console 400 may optionally be a sealed unit to support cleaning and/or sterilization during and/or between uses. Input control console may optionally be used with one or more sterile drapes to provide a suitable sterile field between input control console 400 and the operator and/or patient.

Input control console 400 is provided as a representative example of possible input control consoles for a computer-assisted medical device, such as the elongate device of FIGS. 1-3B. Additional variations and/or configurations of input control consoles may be found in international Patent Application No. PCT/US2017/039808, filed on Jun. 28, 2017 and entitled "Systems and Methods of Steerable Elongate Device," which is incorporated by reference herein in its entirety.

Figure 5A:
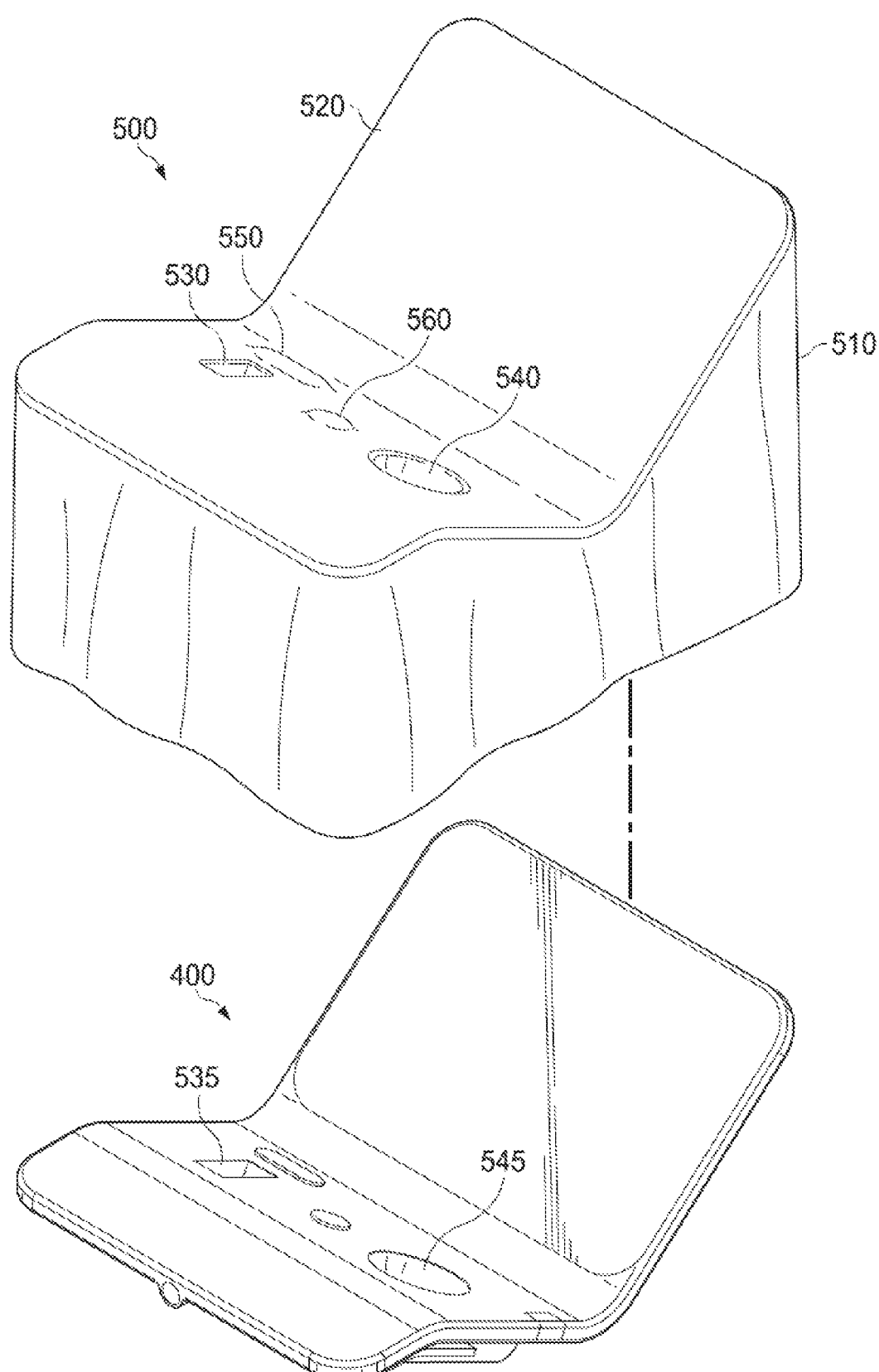
FIGS. 5A and 5B are simplified diagrams of the input control console of FIGS. 4A and 4B and a corresponding drape according to some embodiments.
Figure 5B:
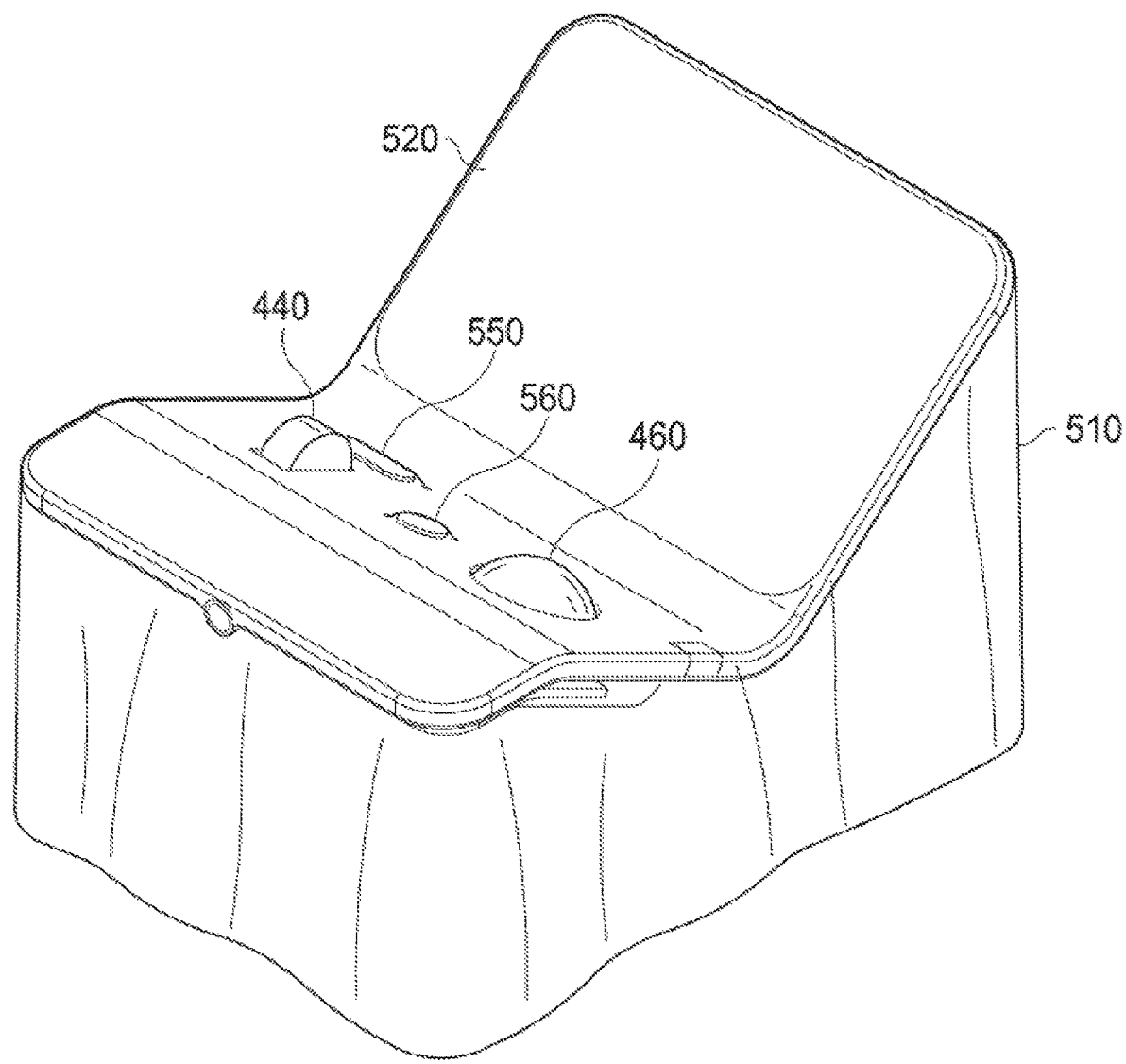

FIGS. 5A and 5B are simplified diagrams of input control console 400 and a corresponding drape 500 according to some embodiments. FIG. 5A shows drape 500 as drape 500 is being installed and FIG. 5B shows drape 500 installed over input control console 400. In some embodiments, the sealing, cleaning, and/or use of input control console in a sterile environment are supported by use of drape 500.

Drape 500 includes a skirt 510 designed to hang down below the upper surface of input control console 400. The length of skirt 510 is sufficient to provide a barrier between data port 480, the one or more paddle arms, and an upper portion of base 495 and the environment including the operator, the patient, and/or the elongate device being controlled. In some examples, skirt 510 helps keep input control console 400 clean and/or provides a sterile field between input control console 400 and the operator, the patient, and/or the elongate device being controlled.

Drape 500 further includes a thermoform panel 520 that is the size and shape of screen 420. Thermoform panel 520 is sufficiently transparent to allow the operator to view screen 420 while drape 500 is in place. In some examples, thermoform panel 520 includes a thermoplastic material. In some examples, the thermoplastic material is conductive so as to allow the operator to use screen 420 as a touch screen through thermoform panel 520.

Drape 500 further includes two integrated moldings 530 and 540 to be inserted into corresponding recesses 535 and 545 in the top of input control console 400 as is discussed in further detail in FIGS. 8-10. The integrated moldings 530 and 540 are configured to receive the moving parts of insertion/retraction control 440 and steering control 460, respectively. In this configuration, the moving parts of insertion/retraction control 440 and/or steering control 460 are able to move freely without interference from drape 500 because drape 500 is not situated between the operator the moving parts of insertion/retraction control 440 and/or steering control 460. The moving parts of insertion/retraction control 440 and steering control 460 are separate from input control console 400 and drape 500 and may be removed and separately cleaned and/or sterilized between uses.

Drape 500 may optionally further include raised regions 550 and 560 configured to fit over a camera cleaning button 430 and passive control button 450, respectively, to place a flexible barrier between the operator and camera cleaning button 430 and passive control button 450 while still allowing their activation by the operator.

Depending upon the embodiment, the moving parts of insertion/retraction control 440 and/or steering control 460 may optionally include one or more retaining mechanisms to keep them seated within moldings 530 and 540, respectively, during operation. In some examples, an axle of the scroll wheel portion of insertion/retraction control 440 snaps into corresponding slots in molding 530. In some examples, the track ball portion of steering control 460 is magnetically held within molding 540 and/or recess 545.

Figure 6:
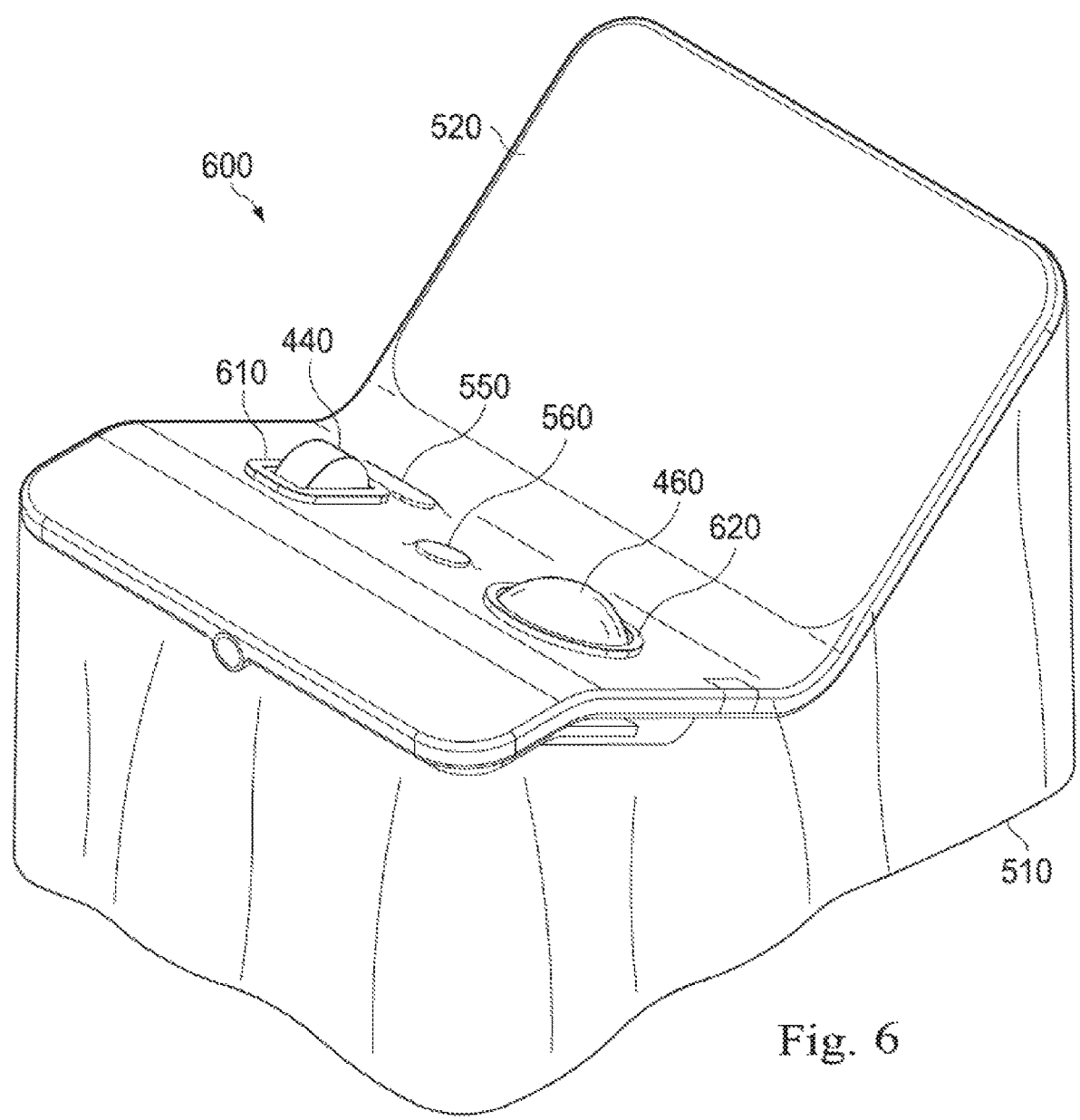
FIG. 6 is a simplified diagram of another input control console with retaining features according to some embodiments.

The moving parts of insertion/retraction control 440 and/or steering control 460 are optionally retained using other mechanisms. FIG. 6 is a simplified diagram of an input control console 600 with retaining features according to some embodiments. As shown in FIG. 6, input control console is substantially similar to input control console 400 with similar controls and features. However, in FIG. 6, the moving parts of insertion/retraction control 440 and/or steering control 460 are retained using retaining rings 610 and 620, respectively. Retaining rings 610 and 620 each include an upper opening that is smaller than the largest diameter of the scroll wheel of insertion/retraction control 440 and the track ball of steering control 460, respectively. The upper openings are positioned just above the respective center lines of the scroll wheel and track ball so that the scroll wheel and track ball are retained in moldings 530 and 540, respectively, during operation. In some examples, retaining rings 610 and 620 may snap fit into moldings 530 and 540, respectively. In some examples, retaining ring 620 may include a twist locking mechanism that mates with molding 540.

Figure 7:
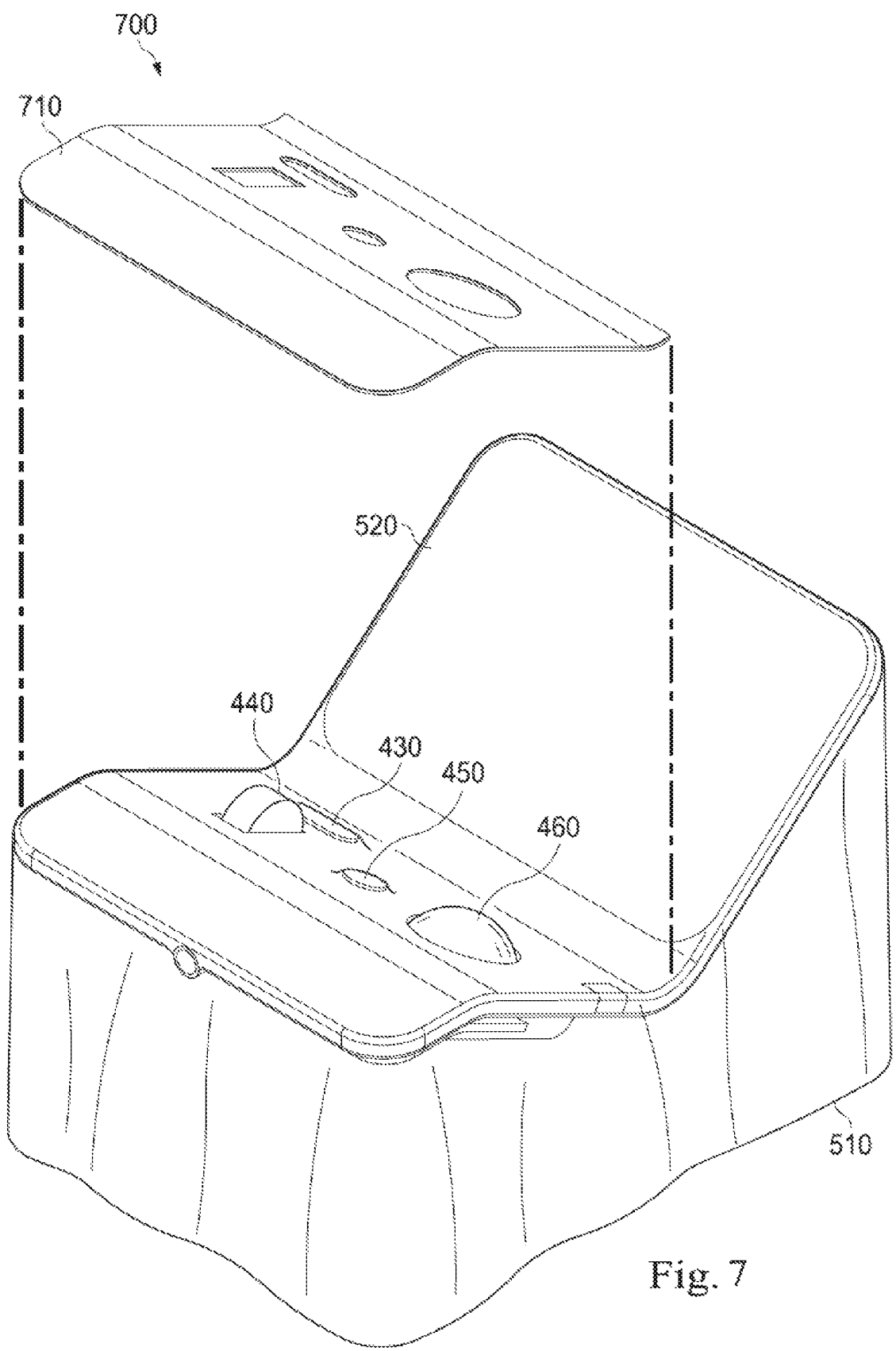
FIG. 7 is a simplified diagram of another input control console with other retaining features according to some embodiments.

FIG. 7 is a simplified diagram of an input control console 700 with other retaining features according to some embodiments. As shown in FIG. 7, the moving parts of insertion/retraction control 440 and/or steering control 460 are held into moldings 530 and 540, respectively, using a snap-in panel 710. Snap-in panel 710 includes openings for the scroll wheel of insertion/retraction control 440 and the track ball of steering control 460 as well as openings to provide operator access to camera cleaning button 430 and/or passive control button 450. In some examples, the openings may optionally include raised bezels. In some examples, snap-in panel 710 may slide and/or snap into one or more grooves, slots, tabs, and/or the like (not shown) located in the upper surface of contoured body 410.

FIG. 8 is a simplified front cut-away view of an input control console 800 according to some embodiments. In some embodiments, input control console 800 is consistent with input control console 400. As shown in FIG. 8, the cut-away of a console body 810 is shown near a centerline of an insertion/retraction control depicted as a scroll wheel, a passive control button, and a steering control depicted as a track ball, although different alignments of the controls, different styles of the controls, and/or different placements of the controls are possible as would be understood in the art.

Console body 810 includes a first recess 820 that may be consistent with recess 535. Recess 820 includes one or more transparent windows 825 associated with one or more sensors (not shown), such as an optical sensor, for sensing and tracking movement of an insertion/retraction control, such as insertion/retraction control 440. And although window 825 is shown at the bottom of recess 820, it may optionally be located at other locations within recess 820 to monitor the insertion/retraction control. In some examples, the one or more sensors may be non-optical (e.g., a magnetic hall effect sensor) and window 825 may be optional. Recess 820 is sufficiently deep so that less than half of the insertion/retraction control extends above an upper surface of console body 810. In some examples, recess 820 is sealed to support cleaning and/or sterilization of input control console 800. In some examples, recess 820 may additionally be associated with one or more contact sensors (not shown) for detecting affirmative contact by the operator with the insertion/retraction control. In some examples, the one or more contact sensors may include one or more capacitive touch, pressure, and/or similar sensors. In some examples, one or more electromagnetic actuators, and/or the like (not shown) may optionally be used to apply haptic feedback to the insertion/retraction control.

Input control console 800 further includes a button 830 that may correspond to passive control button 450. As shown in FIG. 8, button 830 is shown protruding above console body 810, but a flush-mounted or recessed button or other control is also possible.

Console body 810 includes a second recess 840 that may be consistent with recess 545. Recess 840 includes one or more transparent windows 845 associated with one or more sensors (not shown), such as an optical sensor, for sensing and tracking movement of a steering control, such as steering control 460. And although window 845 is shown at the bottom of recess 840, it may optionally be located at other locations within recess 840 to monitor the steering control. In some examples, the one or more sensors may be non-optical (e.g., a magnetic hall effect sensor) and window 845 may be optional. Recess 840 is sufficiently deep so that less than half of the steering control extends above an upper surface of console body 810. In some examples, recess 840 may include retention magnets (not shown) such that a corresponding steering control, such as steering control 890, can include magnetic or ferromagnetic material which aids in retaining the steering control within recess 840. In some examples, recess 840 is sealed to support cleaning and/or sterilization of input control console 800. In some examples, recess 840 may additionally be associated with one or more contact sensors (not shown) for detecting affirmative contact by the operator with the steering control. In some examples, the one or more contact sensors may include one or more capacitive touch, pressure, and/or similar sensors. In some examples, one or more electromagnetic actuators, and/or the like (not shown) may optionally be used to apply haptic feedback to the steering control.

FIG. 8 also shows the integrated features of a drape 850. In some examples, drape 850 is consistent with drape 500. For example, one of the integrated features is a raised region 855 located over button 830, which may be consistent with raised region 560. In some examples, when button 830 is flush or recessed, raised region. 855 is optional and may be omitted.

FIG. 8 shows drape 850 with an integrated molding 860 for receiving the scroll wheel 880 of the insertion/retraction control, however, in some embodiments, molding 860 may be separate from drape 850. In some examples, molding 860 is consistent with molding 530. Molding 860 includes one or more slots or openings 862 that are aligned with the one or more windows 825 in recess 820. Like the one or more windows 825, the one or more openings 862 may be located in positions other than the bottom of molding 860.

Molding 860 further includes an upper lip or flange 864 that extends beyond the edges of recess 820. One or more retention magnets 866 are located at intervals along flange 864 to help position and align molding 860 relative to recess 820. The one or more retention magnets 866 are attracted to one or more corresponding magnets on the upper surface of console body 810 around the edges of recess 820.

Figure 9A:
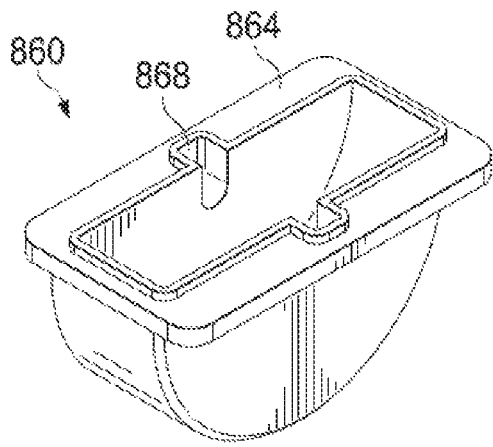
Figure 9B:
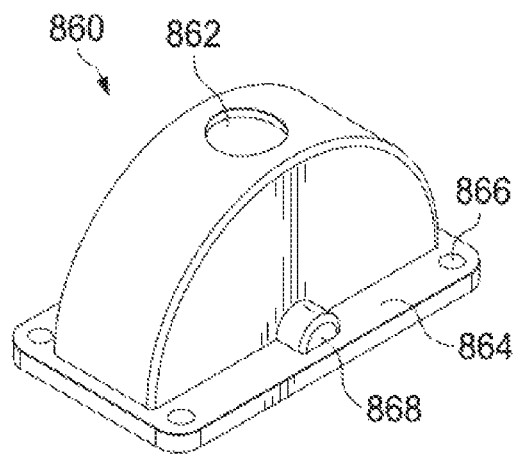

Molding 860 further includes an axle recess 868 on each side to receive an axle 885 of scroll wheel 880. Each axle recess 868 includes one or more ridges or detents and/or a narrow upper opening so that axle 885 may be snapped into axle recesses 868, yet still allow unencumbered rotational motion of scroll wheel 880. In some examples, axle recess 868 may include retention magnets and axle 885 may include magnetic or ferromagnetic material to aid in retaining axle 885 within axle recess 868. Further details of molding 860 are shown in FIGS. 9A and 9B, which show simplified perspective views of molding 860 and its various features.

Figure 10A:
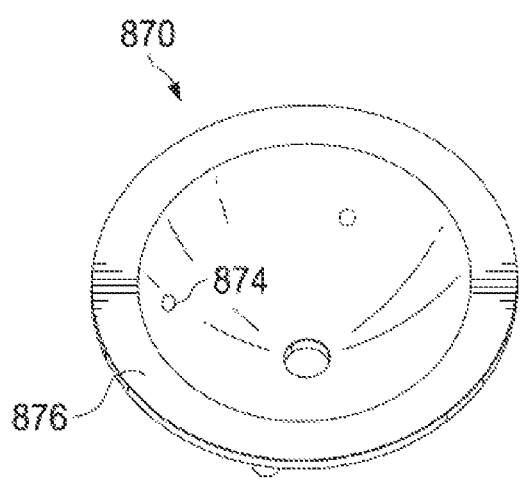
Figure 10B:
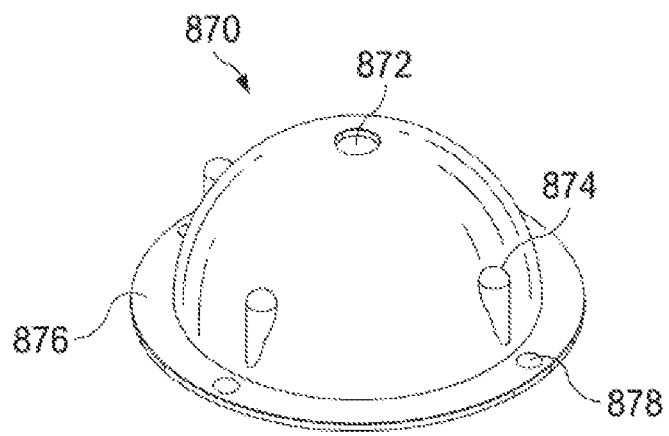

FIG. 8 further shows drape 850 with an integrated molding 870 for receiving a track ball. 890 of the steering control, however, in some embodiments, molding 870 may be separate from drape 850. In some examples, molding 870 is consistent with molding 540. Referring to FIGS. 10A and 10B, molding 870 includes one or more slots or openings 872 that are aligned with the one or more windows 845 in recess 840. Like the one or more windows 845, the one or more openings 872 may be located in positions other than the bottom of molding 870.

Molding 870 further includes an upper lip or flange 876 that extends beyond the edges of recess 840. One or more retention magnets 878 are located at intervals along flange 876 to help position and align molding 870 relative to recess 840. The one or more retention magnets 878 are attracted to one or more corresponding magnets on the upper surface of console body 810 around the edges of recess 840.

Molding 870 further includes one or more bearings and/or raised protrusions 874 for suspending track ball 890 above molding 870 and to allow less restricted rotational movement of track ball 890 relative to molding 870. Further details of molding 870 are shown in FIGS. 10A and 10B, which show simplified perspective views of molding 870 and its various features.

FIG. 11 is a simplified diagram of a method 11 of preparing and using an input control console according to some embodiments. The method 1100 is illustrated in FIG. 11 as a set of operations or processes 1110-1170. Not all of the illustrated processes 1110-1170 may be performed in all embodiments of method 1100. Additionally, one or more processes that are not expressly illustrated in FIG. 11 may be included before, after, in between, or as part of the processes 1110-1170. In some embodiments, the input control console of processes 1110-1170 is consistent with input control console 400, 800 and/or 900 (described with reference to FIGS. 12 and 13) and the drape with integrated moldings of processes 1110-1170 is consistent with drape 500 and/or 850. In some examples, one or more of processes 1110, 1150, and/or 1160 are optional and may be omitted.

At an optional process 1110, an input control console, such as input control console 400 or 800, is cleaned. In some examples, the input control console may be cleaned by wiping down the outer surfaces and/or wiping out any materials, dust, dirt, and/or debris in one or more recesses, such as one or more of recesses 535, 545, 820, and/or 840. In some examples, the one or more recesses should be sufficiently clean so that one or more corresponding moldings 530, 540, 860, and/or 870 may be inserted into the one or more recesses and/or one or more sensor windows, such as openings 862 and/or 872 are clean enough to permit proper sensing of motion in the input controls. In some examples, process 1110 may further include cleaning the moving parts (e.g., a scroll wheel and/or a track ball) of one or more input controls. In some examples, the cleaning of process 1110 may include sterilizing.

At a process 1120, a drape, such as drape 500 and/or 850 is installed. The drape is installed by placing it over the input control console and aligning the various features. Aligning the features includes aligning a thermoform panel, such as thermoform panel 520, with a display screen of the input control console, such as screen 420. Aligning of the features further includes aligning one or more moldings, such as moldings 530, 540, 860, and/or 870 with the one or more recesses in the input control console. In some examples, when the one or more moldings are integrated into the drape, the moldings are aligned along with the drape. In some examples, when the one or more moldings are separate from the drape, corresponding openings in the drape are aligned with the one or more recesses and then the one or more moldings are inserted into the recesses through the openings in the drape. In some examples, the one or more moldings may further help to hold the drape in place over the input control console. In some examples, when the drape includes one or more raised regions, such as raised regions 550 and/or 560, the one or more raised regions are aligned with one or more respective controls on the input control console.

At a process 1130, one or more magnets, such as the one or more magnets 866 and/or 878, on each of the moldings are seated. The one or more magnets may be seated by aligning them with one or more corresponding magnets in the input control console. In some examples, the one or more magnets may facilitate and/or help align the one or more moldings relative to the one or more recesses.

At a process 1140, one or more input controls are installed into the one or more moldings. In some examples, when the one or more input controls include a scroll wheel, such as scroll wheel 880, an axle, such as axle 885, may be snapped into one or more axle recesses, such as axle recesses 868. In some examples, when the one or more input controls include a track ball, such as track ball 890, the track ball may be rested on one or more bearings and/or raised protrusions, such as the one or more bearings and/or raised protrusions 874, of a corresponding molding.

At an optional process 1150, one or more retaining devices are added to help retain the one or more input controls installed during process 1140 in their corresponding moldings. In some examples, when the one or more retaining devices include one or more retaining rings, such as retaining rings 610 and/or 620, the one or more retaining rings are snapped into place around the input controls and/or twist locked into place. In some examples, when the one or more retaining devices include a snap-in panel, such as snap-in panel 710, the snap-in panel is snapped into place on the top of the input control console and around the one or more input controls.

At an optional process 1160, a height and/or an angle of the input control console is adjusted. In some examples, one or more paddle arms, such as the one or more paddle levers 490, are used to adjust a height and/or an angle of the input control console relative to a base of the input control console, such as base 495.

At a process 1170, a corresponding device, such as an elongate device, is operated using the input control console. In some examples, an insertion/retraction control, such as insertion/retraction control 440 and/or scroll wheel 880, are manipulated by an operator to control an insertion depth of the elongate device. In some examples, a steering control, such as steering control 460 and/or track ball 890, are manipulated by the operator to control a pitch and/or yaw of a distal end of the elongate device. In some examples, one or more additional controls, such as camera cleaning button 430, passive control button 450 and/or 830, and/or emergency stop button 470 may additionally be operated. In some examples, control of the corresponding device may include viewing and/or interacting with information displayed on a display screen, such as screen 420, using, for example, touch screen capabilities of the display screen. In some examples, when the input control console determines that the operator is no longer affirmatively in contact with the one or more input controls installed during process 1140, such as by using one or capacitive touch and/or pressure sensors, the elongate device may be placed in a lock mode. Processes 1150 and 1160 may then be repeated as desired.

As discussed above and further emphasized here, FIG. 11 is merely an example which should not unduly limit the scope of the claims. One of ordinary skill in the art would recognize many variations, alternatives, and modifications. In some embodiments, method 1100 may further include one or more processes for preparing an elongate device for a particular operator, patient, and/or procedure. In some examples, a data port, such as data port 480, may be used to provide operator, patient, and/or procedure specific information to the input control console. In some examples, a flash drive may be inserted into the data port either before or after the drape is installed during process 1120. In some examples, a process for mounting and/or otherwise coupling an elongate device, such as elongate device 104 and/or 200 may also be included.

FIGS. 12 and 13 are simplified perspective diagrams of another input control console 900 according to some embodiments. FIG. 12 shows the input control console 900 in an operable condition, and FIG. 13 shows the input control console 900 in a cleaning condition, with some of the removable input controls displaced. The input control console 900 has many similarities to the input control consoles 400, 600, and 800 described herein. For ease of reference, not all similar features will be re-described with reference to the input control console 900, recognizing that the descriptions of input control consoles 400, 600, and 800 also apply to the input control console 900. In this implementation, a top surface 902 of the input control console 900 includes various input controls including the camera cleaning button 430, the insertion/retraction control 440, the passive control button 450, and the steering control 460. Some embodiments do not include one or more of the input controls, such as for example, the camera cleaning button 430, and yet other embodiments include additional input controls. The insertion/retraction control 440 and the steering control 460 are removably disposed in the recesses 535 and 545, respectively as shown in FIG. 13.

In some embodiments, the complete input control console 900 is a sealed unit. In some embodiments, the input control console 900 can be a liquid resistant unit where components, recesses, or breaks may be fully or partially sealed to liquid leakage. Accordingly, the input control console 900 is protected from spilled liquids, and can be sprayed and easily wiped for cleaning and sterilization. In some embodiments, the recesses 535 and 545 are sealed with the surface 902 of the input control console 900 so as to form a continuous, unbroken surface. The passive control button 450 and/or the camera cleaning button 430 may be sealed using conventional seals such as for example, a silicon gasket. In some embodiments, the passive control button 450 and/or the camera cleaning button 430 may be formed of a touchpad or conductive button so to be flush with and a part of the top surface 902. This may further simple cleaning of the top surface 902 of the input control console 900.

FIGS. 12 and 13 show that the insertion/retraction control 440 and the steering control 460 may be removably disposed within the recesses 535 and 545. Removal may further simplify cleaning and sterilization of the input controls, as well as the recesses 535 and 545.

In this embodiment, the insertion/retraction control 440 is a part of a removable control assembly 904 that includes the insertion/retraction control 440 as a scroll wheel, a recess bracket 906, and an integrated axle 908. The recess bracket 906 is sized to fit along the edge of the recess 535 and maintain the insertion/retraction control 440 in position for operation. The recess bracket 906 may also support the axle 908 about which the insertion/retraction control 440 rotates. The control assembly 904 fits within the corresponding recess 535 and may be removed for cleaning or replacement.

A ring or lip 910 may extend around an edge of the recess 545. This may be sealed to and/or form a part of the surface 902, or may be removably attached to the surface 902. In this implementation, the removable steering control 460 may fit through the ring or lip 910 and into the recess 545. In some embodiments, half or more of the steering control 460 protrudes above the top surface 902. Although the ring or lip 910 and the recess bracket 906 are shown in FIG. 12 as protruding above the top surface 902, in some embodiments the ring or lip 910 and the recess bracket 906 are flush with the top surface 902, and in yet other embodiments, the ring or lip 910 and the recess bracket 906 are recessed below the top surface 902. In the recess 545, the steering control 460 may float on one or more bearings and/or raised protrusions 874 (FIG. 8) for suspending the steering control 460. The bearing or raised protrusions may be roller bearings, point contact bearings, or other bearings or protrusions that provide support to the steering control 460 by rolling or providing non-rolling protrusion contacts, as described with reference to FIG. 8, A magnet fixture (not shown) may be provided to simplify removal of the steering control 460 from the recess 545. The magnet fixture may include magnets powerful enough to overcome the weight of the steering control 460 and other forces holding the steering control 460 in the recess 545. It may be used to lift the steering control 460 from the recess.

As described above with reference to FIG. 8, each recess 535 and 545 may include or be formed of an opaque cup. The opaque cup may be sealed and may include one or more transparent regions or windows. Some embodiments include an entirely transparent cup. The transparent regions or windows or the entirely transparent cup may be associated with one or more sensors, such as optical sensors, magnetic Hall effect sensors, or other types of sensors for sensing and tracking movement of the insertion retraction control 440 and/or the steering control 460, as described herein. In some embodiments, the ring or lip 910 is merely the upper edge of the opaque or transparent cup and is flush with the top surface 902. In some embodiments, retention magnets may be disposed within or adjacent the recesses 535 and 545 to help retain e steering control 460 and/or the removable control assembly 904 therein. As described with reference to FIG. 8, in some examples, the recesses 535, 545 may be associated with one or more contact sensors for detecting affirmative contact by the operator with the steering control 460 and/or the insertion/retraction control 440. Some examples of the input control console 900 include one or more electromagnetic actuators and/or the like to apply haptic feedback to the steering control.

EXAMPLES

1. A drape for an input control console for an elongate device, the drape comprising:

a transparent thermoform panel configured to fit over a display integrated into the input control console;

a first integrated molding configured to fit into a first recess in the input control console and to receive a first input control; and a skirt.

2. The drape of example 1, wherein the thermoform panel is conductive to allow touch sensitive access to the display.

3. The drape of any of examples 1-2, further comprising a second molding configured to fit into a second recess in the input control console and to receive a second input control.

4. The drape of any of examples 1-3, wherein the first integrated molding includes an upper lip with one or more magnets for attaching the first integrated molding to a top of the input control console.

5. The drape of any of examples 1-4, further comprising a retaining ring configured to hold the first input control in the first recess.

6. The drape of any of examples 1-5, wherein the first integrated molding includes one or more slots positioned to be aligned with one or more sensors in the input control console.

7. The drape of any of examples 1-6, wherein the first integrated molding includes an axle recess on each side configured to receive an axle.

8. The drape of any of examples 1-7, wherein the first integrated molding includes a plurality of bearings or raised protrusion on an inner surface configured to suspend the first input control.

9. A method for protecting an input control console, the method comprising:

aligning a drape over the input control console by:
aligning a transparent thermoform panel over a display screen integrated into the input control console;
inserting at least one molding integrated into the drape into at least one recess of the input control console;
inserting at least one input control in the at least one molding; and
positioning a skirt of the drape around the input control console,
wherein the at least one molding allows for sensing motion of the at least one input control using one or more sensors within the input control console.

10. The method of example 9, further comprising fitting an axle into an axle recess, wherein the axle recess is included in the at least one molding.

11. The method of any of examples 9-10, further comprising snapping a retaining ring or a snap-in panel into the at least one recess to hold the at least one input control within the recess.

One or more elements in embodiments of the invention (e.g., the processing of signals received from the input controls and/or control of the elongate device) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media, examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A drape for an input control console for an elongate device, the drape comprising:
a transparent panel configured to fit over a display integrated into the input control console;
a first molding configured to fit into a first recess in the input control console and to receive a first input control; and
a skirt.

2. The drape of claim 1, wherein the transparent panel is conductive to allow touch sensitive access to the display.

3. The drape of claim 1, further comprising a second molding configured to fit into a second recess in the input control console and to receive a second input control.

4. The drape of claim 1, wherein the first molding includes an upper lip with one or more magnets for attaching the first molding to a top of the input control console.

5. The drape of claim 1, further comprising a retaining ring configured to hold the first input control in the first recess.

6. The drape of claim 1, wherein the first molding includes one or more slots positioned to be aligned with one or more sensors in the input control console.

7. The drape of claim 1, wherein the first molding includes an axle recess on each side configured to receive an axle.

8. The drape of claim 1, wherein the first molding comprises a plurality of bearings configured to support the first input control in the first molding.

9. The drape of claim 1, wherein the first molding comprises a raised protrusion configured to suspend the first input control in the first molding.

10. The drape of claim 1, wherein the transparent panel comprises a thermoform panel.

11. A system comprising:
an input control console for an elongate device, wherein the input control console comprises a display integrated into the input control console and a recess;
a panel configured to fit over the display;
a molding configured to fit into the recess and to receive an input control; and
a skirt.

12. The system of claim 11, wherein the panel is conductive to allow touch sensitive access to the display.

13. The system of claim 11, wherein the input control console comprises a second recess, and wherein the system further comprises a second molding configured to fit into the second recess and to receive a second input control.

14. A drape for an input control console for an elongate device, the drape comprising:
- a first portion comprising a transparent panel configured to fit over a display integrated into the input control console;
- a second portion integral with the first portion, the second portion comprising an opening disposed and shaped to fit about a recess formed in the input control console when the first portion is fit over the display, the opening being sized to receive an input control introducible into the recess; and
- a skirt extending from the second portion.

15. The drape of claim 14, wherein the transparent panel is conductive to allow touch sensitive access to the display.

16. The drape of claim 14, further comprising a second opening disposed and shaped to fit about a second recess formed in the input control console when the first portion is fit over the display, the second opening being sized to receive a second input control introducible into the recess.

17. The drape of claim 16, wherein the opening and the second opening have different shapes.

18. The drape of claim 14, wherein the opening is sized to interface with a molding insertable into the recess formed in the input control console to hold the drape in place.

19. The drape of claim 14, comprising one or more raised regions adjacent the opening and alignable with raised controls on the input control console.

20. The drape of claim 14, wherein the transparent panel comprises a thermoform panel.

* * * * *